US009609286B2

(12) United States Patent
Ichihashi

(10) Patent No.: US 9,609,286 B2
(45) Date of Patent: Mar. 28, 2017

(54) ENDOSCOPE

(71) Applicant: Olympus Corporation, Tokyo (JP)

(72) Inventor: Masaki Ichihashi, Tokyo (JP)

(73) Assignee: Olympus Corporation, Hachioji-shi, Tokyo (JP)

( * ) Notice: Subject to any disclaimer, the term of this patent is extended or adjusted under 35 U.S.C. 154(b) by 463 days.

(21) Appl. No.: 14/087,627

(22) Filed: Nov. 22, 2013

(65) Prior Publication Data
US 2014/0078287 A1   Mar. 20, 2014

Related U.S. Application Data

(63) Continuation of application No. PCT/JP2011/061976, filed on May 25, 2011.

(51) Int. Cl.
| H04N 7/18 | (2006.01) |
| A61B 1/05 | (2006.01) |
| G02B 23/24 | (2006.01) |
| A61B 1/00 | (2006.01) |
| A61B 1/005 | (2006.01) |
| A61B 1/06 | (2006.01) |
| H04N 5/225 | (2006.01) |

(52) U.S. Cl.
CPC ............ *H04N 7/183* (2013.01); *A61B 1/005* (2013.01); *A61B 1/00009* (2013.01); *A61B 1/00027* (2013.01); *A61B 1/00045* (2013.01); *A61B 1/00071* (2013.01); *A61B 1/00096* (2013.01); *A61B 1/00101* (2013.01); *A61B 1/051* (2013.01); *A61B 1/0661* (2013.01); *A61B 1/0676* (2013.01); *A61B 1/0684* (2013.01); *G02B 23/2476* (2013.01); *G02B 23/2492* (2013.01); *A61B 1/00034* (2013.01); *H04N 2005/2255* (2013.01)

(58) Field of Classification Search
CPC ............ A61B 1/00071; A61B 1/00009; A61B 1/00027; A61B 1/00034; A61B 1/00045; A61B 1/00096; A61B 1/00101; A61B 1/005; A61B 1/051; A61B 1/0661; A61B 1/0676; A61B 1/0684; H04N 2005/2255; H04N 7/183; G02B 23/2476; G02B 23/2492

See application file for complete search history.

(56) References Cited

U.S. PATENT DOCUMENTS

| 6,796,939 B1* | 9/2004 | Hirata | ............... A61B 1/00036 600/109 |
| 2003/0216614 A1* | 11/2003 | Sawai | ............... A61B 1/05 600/110 |

FOREIGN PATENT DOCUMENTS

| JP | 01-265219 A | 10/1989 |
| JP | 2001-075021 A | 3/2001 |
| JP | 2005-296259 A | 10/2005 |
| JP | 2007-152020 A | 6/2007 |

(Continued)

OTHER PUBLICATIONS

International Search Report for PCT/JP2011/061976, mailing date Mar. 6, 2012.

*Primary Examiner* — Mohammed Rahaman
(74) *Attorney, Agent, or Firm* — Arent Fox LLP

(57) ABSTRACT

In the endoscope of the present invention, first electronic components and second electronic components are provided inside an elongated insertion portion, and a solid ground pattern that extends over a greater range than the first electronic components is interposed between the first electronic components and the second electronic components.

4 Claims, 16 Drawing Sheets

(56) References Cited

FOREIGN PATENT DOCUMENTS

| | | |
|---|---|---|
| JP | 2007-201895 A | 8/2007 |
| JP | 2008-292730 A | 12/2008 |

* cited by examiner

ENDOSCOPE

The present application is a Continuation Application of PCT Patent Application No. PCT/JP2011/061976, filed May 25, 2011, the contents of which are incorporated herein by reference.

BACKGROUND OF THE INVENTION

Field of the Invention

The present invention relates to an endoscope.

Technical Background

Conventionally, an endoscope is known that is used for observing locations that are difficult for an observer to view directly, such as the interior of an observation subject and the like. An endoscope is provided with an elongated insertion portion and an image acquisition portion that is provided at a distal end of the insertion portion.

Endoscopes can be broadly grouped into medical endoscopes that are used to observe the interior of a human body, and industrial endoscopes that are used to observe the interior of machinery.

In some cases, industrial endoscopes are employed in environments where there is a possibility that the environment may be filled with an explosive atmosphere such as boilers, chemical plants, and the engines of automobiles and aircraft and the like. For example, in Japanese Unexamined Patent Application, First Publication (JP-A) No. 2007-152020, an endoscope is disclosed that it is assumed will be used in an environment surrounded by inflammable gas or dust.

According to the endoscope described in JP-A No. 2007-152020, because the control unit, the insertion portion, and the optical adaptor have an intrinsically safe explosion-proof construction, they are able to be used in locations where there is a danger of an explosion occurring.

SUMMARY OF THE INVENTION

A first aspect of the present invention is an endoscope having: an elongated insertion portion; a main unit to which one end of the insertion portion is attached; first electronic components that are provided inside the insertion portion; second electronic components that are provided inside the insertion portion and are supplied with drive power from a separate system from that used for the first electronic components; a first substrate that is formed as a thin plate or film, and on one surface of which in the thickness direction thereof the first electronic components are packaged; a second substrate that is formed as a thin plate or film, and on one surface of which in the thickness direction thereof the second electronic components are packaged; a plurality of power limiting portions that limit to a predetermined value or less the drive power that they supply to the first electronic components and the second electronic components respectively via mutually different systems; a first wiring of which at least a portion is placed inside the insertion portion, and that electrically connects together one of the power limiting portions and the first electronic components and supplies drive power to the first electronic components; and a second wiring of which at least a portion is placed inside the insertion portion, and that electrically connects together another of the power limiting portions and the second electronic components and supplies drive power to the second electronic components, wherein the first substrate has a solid ground pattern that is formed either on the opposite surface of the first substrate from the surface thereof on which the first electronic components are packaged or else inside the first substrate and that, when viewed from the thickness direction of the first substrate, extends over a broader area than the first electronic components.

It is also possible for the first substrate and the second substrate to be integrated into a multi-layer substrate by mutually superimposing the first substrate and the second substrate in the thickness direction thereof, and for the ground pattern to be interposed between the first parts and the second parts.

It is also possible for the first substrate and the second substrate to be formed by a flexible substrate that is continuous in the surface direction thereof, and for the first electronic components and the second electronic components to be packaged on a one surface in the thickness direction of the continuous flexible substrate, and for the flexible substrate to be folded in half between the first electronic components and the second electronic components such that the ground pattern is positioned between the first electronic components and the second electronic components, and is placed inside the insertion portion.

It is also possible for there to be provided a metal supporting body that is located at a distal portion of the insertion portion and supports the first substrate and the second substrate, and for the ground of the first electronic components and the second electronic components to be electrically connected to the supporting body, and for the first electronic components and the second electronic components to be thermally connected to the supporting body.

A second aspect of the present invention is an endoscope having: an elongated insertion portion; a main unit to which one end of the insertion portion is attached; a first electronic instrument that is provided inside the insertion portion; a second electronic instrument that is provided inside the insertion portion and is supplied with drive power from a separate system from that used for the first electronic instrument; a plurality of power limiting portions that limit to a predetermined value or less the drive power that they supply to the first electronic instrument and the second electronic instrument respectively via mutually different systems; a first wiring of which at least a portion is placed inside the insertion portion, and that electrically connects together one of the power limiting portions and the first electronic instrument and supplies drive power to the first electronic instrument; a second wiring of which at least a portion is placed inside the insertion portion, and that electrically connects together another of the power limiting portions and the second electronic instrument and supplies drive power to the second electronic instrument; and a system separating component that electrically separates the first electronic instrument and the first wiring from the second electronic instrument and the second wiring such that they conform to an intrinsically safe explosion-proof structure, wherein the system separating component has an insulating covering component that covers the entire circumference of at least one of the first electronic instrument and the first wiring, and the second electronic instrument and the second wiring inside the insertion portion from one end of the insertion portion as far as the other end thereof.

It is preferable for the thickness of the insulating covering component to be 0.5 mm or more.

It is also possible for the insulating covering component to have: a first insulating component that covers the entire outer circumference of the first electronic instrument; and a second insulating component that overlaps with the first insulating component in the thickness direction of the first insulating component and covers the entire circumference of the first wiring.

In this case, in the area where the first insulating component and the second insulating component overlap each other, it is preferable for the shortest distance measured along the contact surface between the first insulating component and the second insulating component to be at least 1.5 mm.

A third aspect of the present invention is an endoscope having: an elongated insertion portion; a main unit to which one end of the insertion portion is attached; a first electronic instrument that is provided inside the insertion portion; a second electronic instrument that is provided inside the insertion portion and is supplied with drive power from a separate system from that used for the first electronic instrument; a plurality of power limiting portions that limit to a predetermined value or less the drive power that they supply to the first electronic instrument and the second electronic instrument respectively via mutually different systems; a first wiring of which at least a portion is placed inside the insertion portion, and that electrically connects together one of the power limiting portions and the first electronic instrument and supplies drive power to the first electronic instrument; a second wiring of which at least a portion is placed inside the insertion portion, and that electrically connects together another of the power limiting portions and the second electronic instrument and supplies drive power to the second electronic instrument; and a system separating component that electrically separates the first electronic instrument and the first wiring from the second electronic instrument and the second wiring such that they conform to an intrinsically safe explosion-proof structure, wherein the system separating component has a ground wire that is interposed between the first electronic instrument and the first wiring, and the second electronic instrument and the second wiring without coming into contact with either of them, and is in the form of a continuous conductive wire that extends from one end of the insertion portion to the other end thereof, and that forms a common ground wire for both the first electronic instrument and the second electronic instrument.

It is also possible for the ground wire to have: a distal end rigid portion that is made from metal and is provided at the distal portion of the insertion portion, and that supports the first electronic instrument and the second electronic instrument; and a heat discharge wire that is made from a continuous metal wire, and whose distal end is fixed to the distal end rigid component and whose proximal end is placed inside the main unit.

It is also possible for the ground wire to have a shield that is formed by a conductive body that covers the entire circumference of either the first wiring or the second wiring.

It is also possible for a rechargeable battery that is electrically connected to each of the power limiting portions and serves as a power supply for the first electronic instrument and the second electronic instrument to be provided inside the main unit, and for the ground wire to be connected to a negative terminal of the rechargeable battery.

It is also possible for the ground wire to be earthed.

DETAILED DESCRIPTION OF THE INVENTION

First Embodiment

An endoscope according to a first embodiment of the present invention will now be described.

Figure 1:
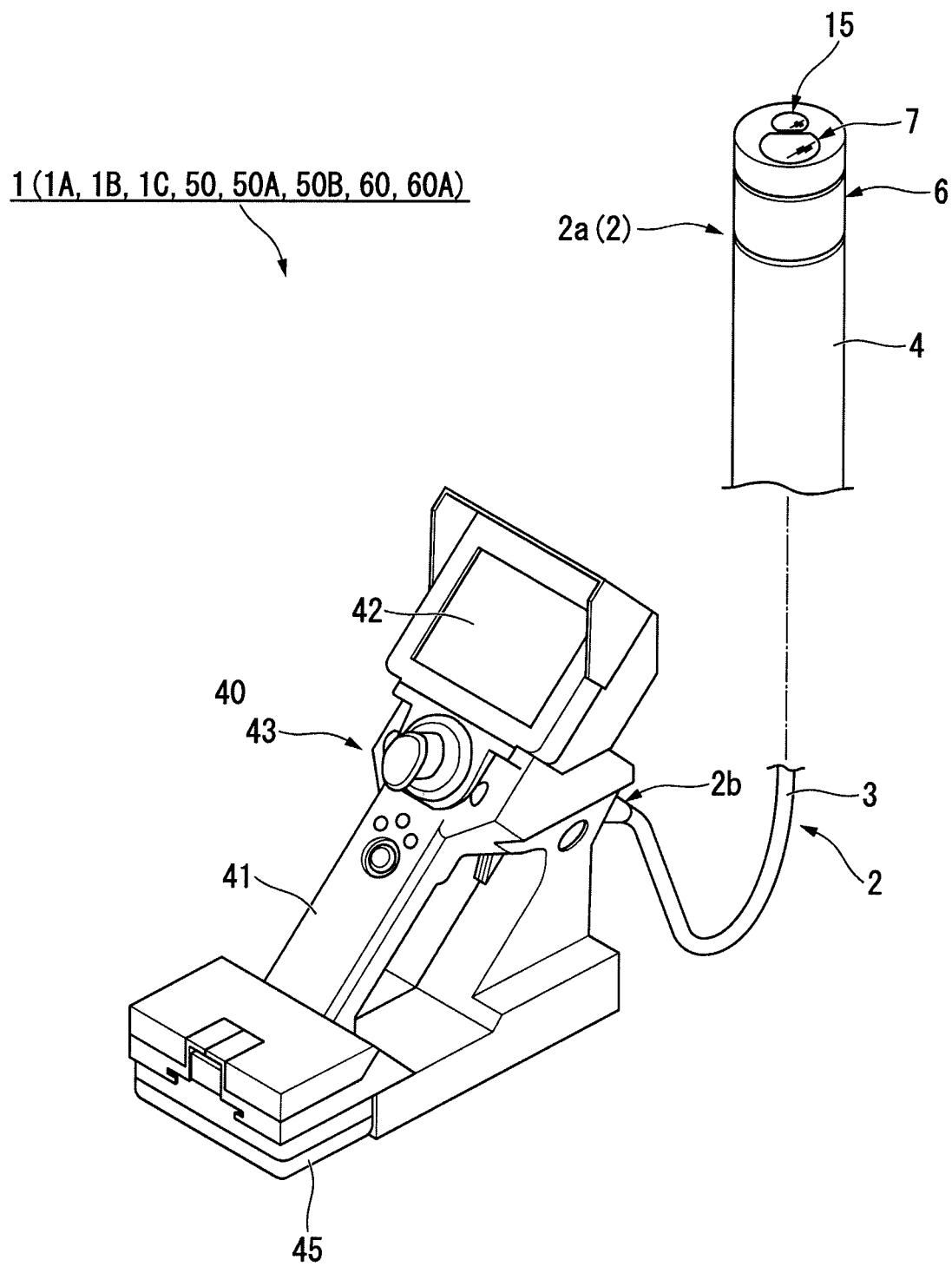
FIG. 1 is an overall view of an endoscope according to a first embodiment of the present invention.
Figure 2:
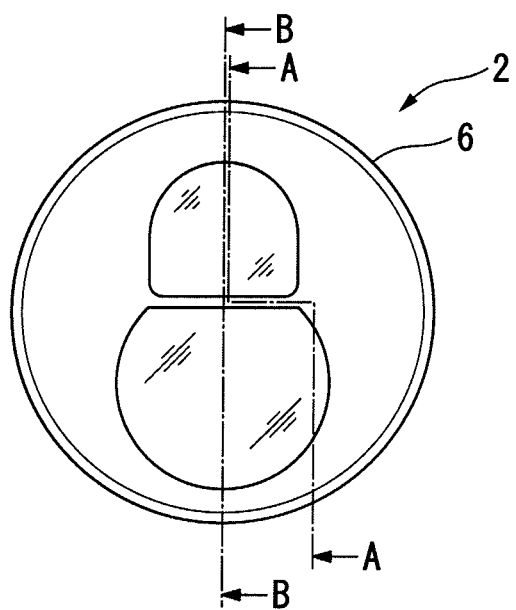
FIG. 2 is a front view showing a distal end surface of an insertion portion of the endoscope.
Figure 3:
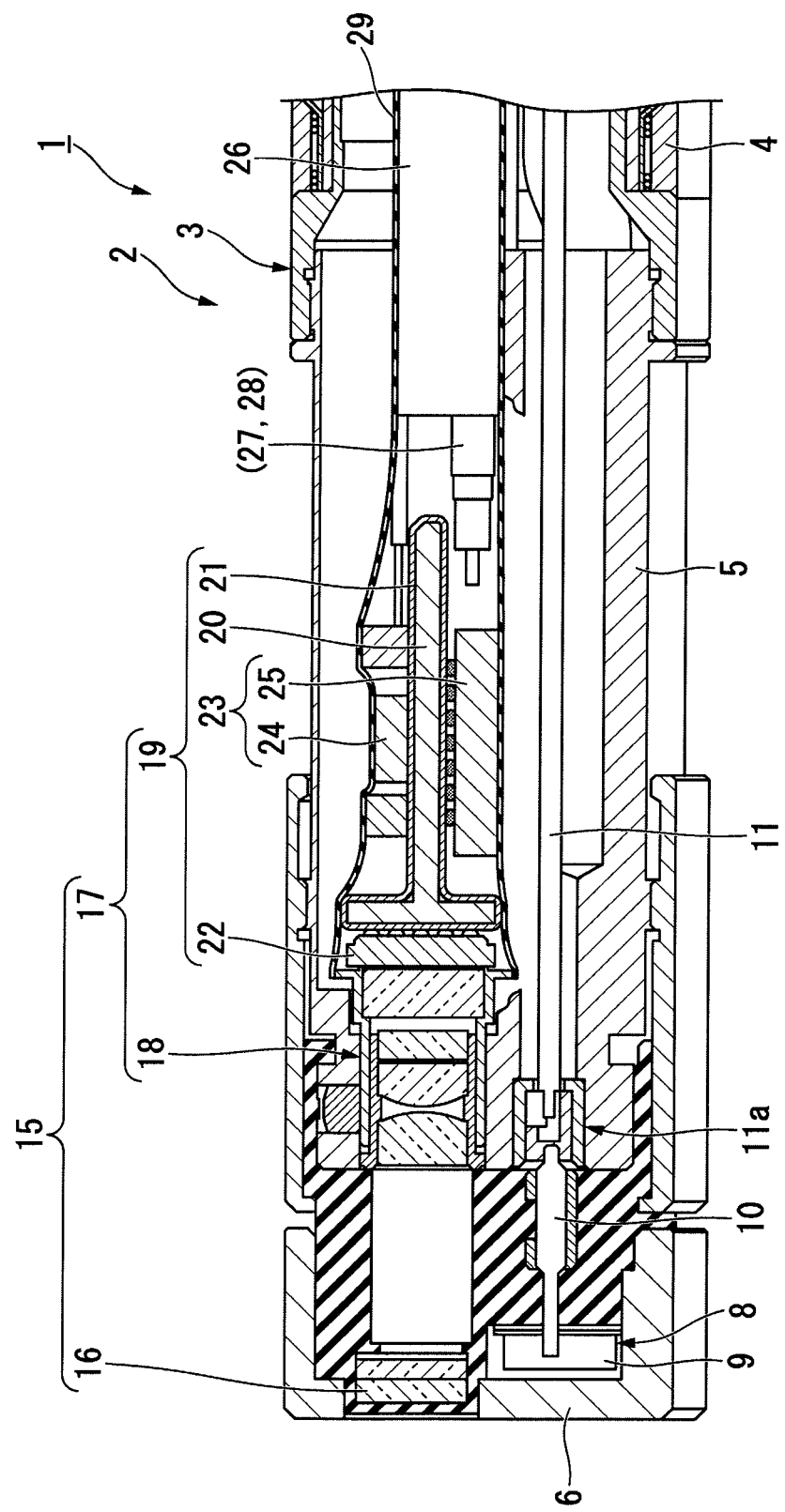
FIG. 3 is a cross-sectional view taken along a line A-A in FIG. 2.
Figure 4:
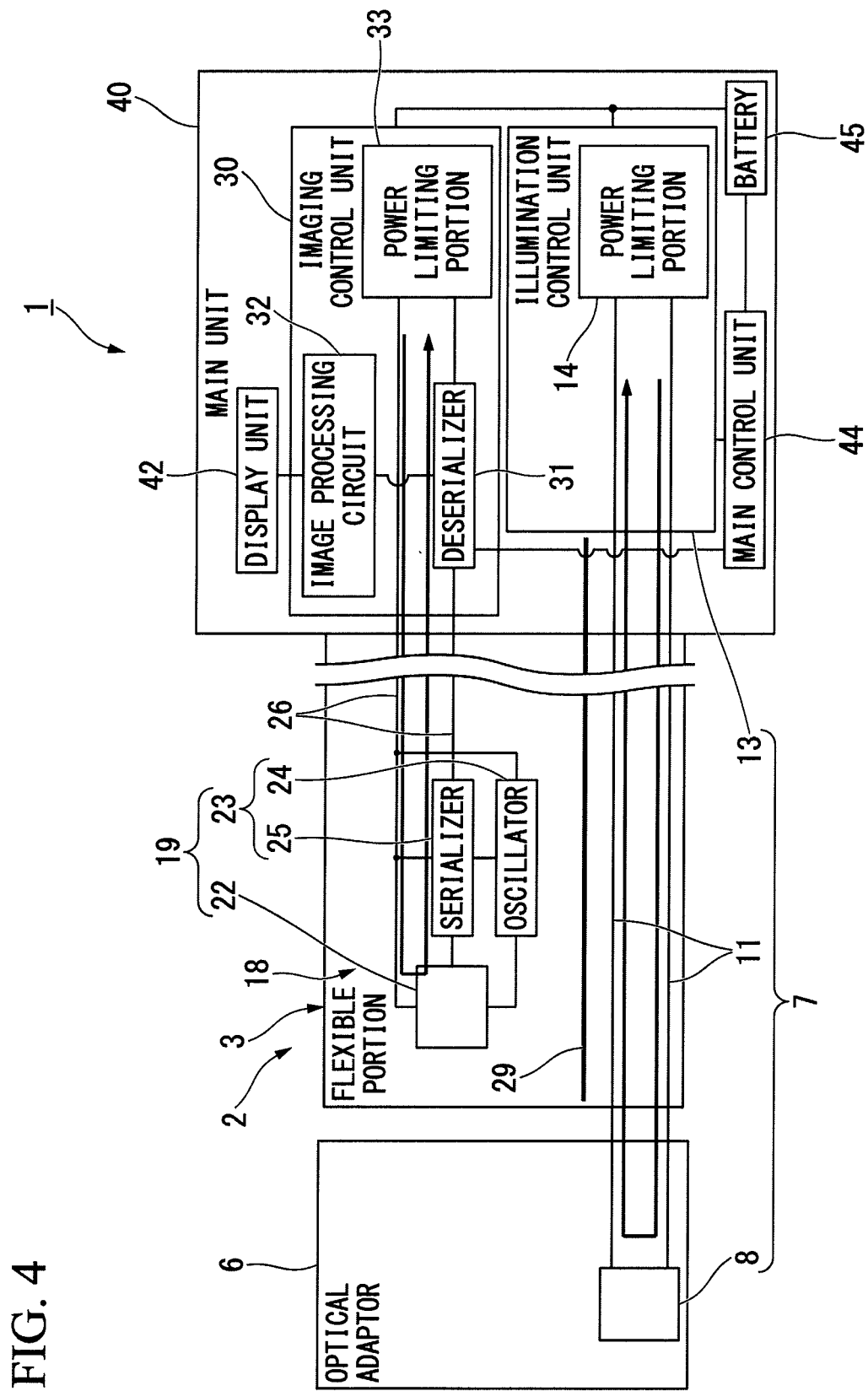
FIG. 4 is a block diagram showing the schematic structure of the endoscope.

FIG. 1 is an overall view of an endoscope 1 of the present embodiment. FIG. 2 is a front view showing a distal end surface of an insertion portion 2 of the endoscope 1. FIG. 3 is a cross-sectional view of the insertion portion taken along a line A-A in FIG. 2. FIG. 4 is a block diagram showing the schematic structure of the endoscope 1.

The endoscope 1 is a device that is used to observe locations that are difficult for an observer to view directly such as the interior of an observation subject and the like. As is shown in FIG. 1, the endoscope 1 is provided with the elongated insertion portion 2 that is inserted from its distal end 2a into an observation subject, and with a main unit 40 to which a proximal end 2b of the insertion portion 2 is fixed.

The insertion portion 2 has a cylindrical flexible portion 3 that is able to be bent, and an optical adaptor 6 that can be removably attached to the flexible portion 3 at the distal end 2a. An illumination portion 7 that irradiates illumination light onto an observation subject, and an image acquisition portion 15 that acquires images of the observation subject onto which the illumination light has been irradiated are provided inside the insertion portion 2. Note that in the present embodiment, the illumination portion 7 and the image acquisition portion 15 are placed inside the optical adaptor 6, the flexible portion 3, and the main unit 40.

As is shown in FIG. 1 and FIG. 3, a bending portion 4 that causes the flexible portion 3 to perform a bending operation, and a distal end rigid component 5 that supports the illumination portion 7 and the image acquisition portion 15 at the distal portion of the bending portion 4 are provided at a distal end of the flexible portion 3. The distal end rigid component 5 is formed, for example, from metal or resin, and has a substantially circular column-shaped external configuration whose central axis matches the direction of the central axis of the insertion portion 2. A through hole through which the illumination portion 7 is inserted, and a through hole through which the image acquisition portion 15 is inserted are formed in the distal end rigid component 5.

As is shown in FIG. 2 and FIG. 3, the optical adaptor 6 protects the distal end surface of the flexible portion 3, and is used to alter the light distribution of the illumination portion 7 and the angle of view of the image acquisition portion 15 and the like. In the present embodiment, a direct-view type of adaptor whose imaging field faces in the direction of the central axis of the insertion portion 2 is employed as an example of the optical adaptor 6. Note that it is also possible to employ what is known as a side-looking type of adaptor whose imaging field faces in a direction that intersects the central axis of the insertion portion 2 as the optical adaptor 6.

As is shown in FIG. 3 and FIG. 4, the illumination portion 7 is provided with a light-emitting unit 8 (i.e., a second electronic instrument) that is disposed inside the optical adaptor 6, wiring 11 (i.e. second wiring) that is placed inside the flexible portion 3 in order to supply drive power to the light-emitting unit 8, and an illumination control unit 13 that is disposed inside the main unit 40.

The light-emitting unit 8 has a light source 9 that is formed, for example, by a light-emitting diode (LED) or a laser diode (LD), and a contact point 10 that is electrically connected to the light source 9.

A distal end of the wiring 11 is placed at the distal end of the flexible portion 3, and a proximal end of the wiring 11 is placed inside the main unit 40. A connecting terminal 11a that is openly exposed to the distal end surface of the flexible portion 3 is fixed to the distal end of the wiring 11. A contact point component having a spring action such that it springs backwards and forwards in the direction of the central axis of the insertion portion 2 is provided on the contact point 10. When the optical adaptor 6 is attached to the insertion portion 2, the light-emitting unit 8 and the wiring 11 are mutually conductive via the contact point 10 and the connecting terminal 11a.

The illumination control unit 13 is an electronic circuit that operates by receiving a power supply from a battery 45 (described below) and is provided with a power limiting portion 14 that, when the light-emitting unit 8 is in a normal state, or when it is in a malfunctioning state, limits the drive power supplied to the light-emitting unit 8 to a predetermined value or less. The illumination control unit 13 is connected to a main control unit 44 (described below) that is provided within the main body 40, and operates in accordance with drive signals emitted from the main control unit 44. In the present embodiment, the drive power supplied to the light-emitting unit 8 is limited by the power limiting portion 14 so that even the illumination portion 7 by itself satisfies the conditions for an intrinsically safe explosion-proof construction (Exia).

As is shown in FIG. 3 and FIG. 4, the image acquisition portion 15 is provided with an optical adaptor objective optical system 16 that is openly exposed to the distal end surface of the optical adaptor 6, an imaging unit 17 (i.e., a first electronic instrument) that is located inside the distal end of the insertion portion 2, wiring 26 whose distal end is connected to the imaging unit 17 and whose proximal end is located inside the main unit 40, and an imaging control unit 30 that is connected to the proximal end of the wiring 26 and that is located inside the main unit 40.

As is shown in FIG. 2 and FIG. 3, the optical adaptor objective optical system 16 is a plate-shaped component that is optically transparent, and is provided in order to alter the viewing direction, the viewing angle, and the observation depth of an observation subject.

As is shown in FIG. 3, the imaging unit 17 has an objective optical system 18 and an imaging circuit portion 19.

The objective optical system 18 is an optical system that guides external light that has been transmitted through the optical adaptor objective optical system 16 to the imaging circuit portion 19, is provided in order to enable images of an observation subject to be acquired in the imaging circuit portion 19.

The imaging circuit portion 19 has a supporting body 20, a circuit substrate 21, an imaging element 22, and an image transmitting portion 23.

The supporting body 20 is formed in a predetermined shape from, for example, resin or metal or the like, and supports the circuit substrate 21 and the respective electronic components that are packaged on the circuit substrate 21.

The circuit substrate 21 is a substrate on which a predetermined wiring pattern is formed and, in the present embodiment, is a flexible printed substrate. The circuit substrate 21 is fixed to an external surface of the supporting body 20.

The imaging element 22 is an electronic component that is packaged on the circuit substrate 21 and is placed on the optical axis of the objective optical system 18. For example, a CCD image sensor (Charge Coupled Device Image Sensor), or a CMOS image sensor (Complementary Metal Oxide Semiconductor Image Sensor) or the like is possible to be employed as the imaging element 22.

The image transmitting portion 23 is packaged on the circuit substrate 21, and has an oscillator 24 that produces clock signals of a predetermined frequency, and a serializer circuit 25 that converts image data acquired by the imaging element 22 into serial data based on the clock signals emitted by the oscillator 24.

The image data that is converted into serial data by the serializer circuit 25 is transmitted to the imaging control unit 30 via the wiring 26.

The wiring 26 has an electricity wire 27 that is used to supply the drive power from the imaging control unit 30 the imaging circuit portion 19, and signal wires 28 that are used to output signals from the imaging circuit portion 19 to the imaging control unit 30.

Drive power for a different system from that of the illumination control unit 13 is supplied to the electricity wire 27 by a power limiting portion 33 (see FIG. 4) that is different from the power limiting portion 14 of the above-described illumination control unit 13.

The number and placement of the signal wires 28 are set based on the transmission system employed in the image transmitting portion 23. When there are at least two signal wires, image data can be serially transmitted using a system in which highs and lows of the potential relative to a reference potential are made to correspond to the 0 and 1 of a digital signal, or a system in which the potential differences between two balanced signal wires are made to correspond to the 0 and 1 of a digital signal.

As is shown in FIG. 3, the imaging circuit portion 19 and the wiring 26 are covered by an insulating covering component 29 (i.e., a system separating component) that is formed from an insulating material.

The insulating covering component 29 is formed by a continuous heat-shrinkable tube that extends inside the insertion portion 2 from the distal end of the insertion portion 2 to the proximal end thereof, and covers the entire circumference of the imaging circuit portion 19 and the wiring 26. Moreover, the insulating covering component 29 is heated after the imaging circuit portion 19 and the wiring 26 have been housed inside it so that it shrinks and becomes tightly adhered to the external surface of the imaging circuit portion 19 and the wiring 26.

The thickness of the insulating covering component 29 is set based on the size of the voltage that is supplied to the imaging circuit portion 19, and on the size of the voltage that is supplied to the light-emitting unit 8. Specifically, the thickness of the insulating covering component 29 is thick enough for a sufficient separation distance obtained from a solid insulating body that it is assumed would prevent short-circuiting between the image acquisition portion 15 and the illumination portion 7 to be secured. More specifically, when the peak of the higher voltage out of the respective drive voltages of the imaging circuit portion 19 and the light-emitting unit 8 is not more than 10V, the thickness of the insulating covering component 29 is set to 0.5 mm or more.

Note that in the present embodiment, the peaks of the respective voltages are set such that the peak of the voltage supplied to the imaging circuit portion 19 and the peak of the drive voltage supplied to the light-emitting unit 8, which are controlled by the power limiting portions 14 and 33, are 6.2V and 7.5V respectively.

As a result of the insulating covering component 29 being provided, the illumination portion 7 and the image acquisition portion 15 satisfy the separation distance stipulated by IEC 60079-11. As a result, within the range of the requirements sought in an intrinsically safe explosion-proof structure, it is possible to be considered that the drive power supplied to the image acquisition portion 15 is not transmitted to the illumination portion 7, and the drive power supplied to the illumination portion 7 is not transmitted to the image acquisition portion 15.

Namely, the insertion portion 2 in which the image acquisition portion 15 and the illumination portion 7 have been placed such that they are insulated from each other by the insulating covering component 29 forms a structure that conforms to the intrinsically safe explosion-proof construction (Exia) standards required of electronic instruments that are used in dangerous locations stipulated as class 0 or class 1 of the explosion proof index in Japan, or in dangerous locations stipulated as Zone 0 or Zone 1 in IEC 60079-10, or in dangerous locations stipulated as Division 1 in the NEC 500 standard in the United States.

As is shown in FIG. 4, the imaging control unit 30 is an electronic circuit that operates by receiving the power supply from the battery 45 (described below) and is provided with a deserializer circuit 31 that reconstructs image data based on serial data transmitted from the serializer circuit 25 via the wiring 26, an image processing circuit 32 that causes reconstructed image data to be displayed on a display unit 42 (described below), and a power limiting portion 33 that, when the electronic components packaged on the circuit substrate 21 are in a normal state, or when they are in a malfunctioning state, limits the drive power supplied to the imaging circuit portion 19 to a predetermined value or less.

The imaging control unit 30 is connected to the main control unit 44 (described below) that is provided within the main body 40, and operates in accordance with drive signals emitted from the main control unit 44. In the present embodiment, the drive power supplied to the imaging circuit portion 19 is limited by the power limiting portion 33 so that the conditions for an intrinsically safe explosion-proof construction (Exia) can be met by the image acquisition portion 15 by itself.

As is shown in FIG. 1 and FIG. 4, the main unit 40 is provided with a gripping portion 41 that is gripped by an observer who is using the endoscope 1, a display unit 42 that is used to display images acquired by the image acquisition portion 15, and an operating input portion 43 that is used by an observer in order to operate the illumination portion 7 and the image acquisition portion 15. In addition, the main control unit 44 that controls the illumination control unit 13 and the imaging control unit 30 based on input signals from the operating input portion 43, and a battery 45 (i.e., a rechargeable battery) in which power is stored and which forms a power supply for the endoscope 1 are provided in the main unit 40.

Operations of the endoscope 1 having the structure described above will now be described.

When the endoscope 1 is put to use, an observer who is using the endoscope 1 guides the distal end of the insertion portion 2 to an observation subject, and irradiates illumination light thereon from the distal portion of the insertion portion 2. Images of the observation subject are then acquired by the image acquisition portion 15 and are displayed on the display unit 42. As a result of this, the observer is able to observe the observation subject using the endoscope 1.

When the endoscope 1 is operating normally, or if it is malfunctioning, because power that is limited by the power limiting portion 14 of the illumination control unit 13 is supplied to the light-emitting unit 8 in the illumination portion 7, and because power that is limited by the power limiting portion 33 of the imaging control unit 30 is supplied to the imaging unit 17 in the image acquisition portion 15, the light-emitting unit 8 and the imaging unit 17 are supplied with drive power from separate systems. Because the illumination portion 7 and the image acquisition portion 15 both individually satisfy intrinsically safe explosion-proof construction (Exia) standards, the requirements for use in the above-described respective dangerous locations can be favorably satisfied by the illumination portion 7 by itself or the image acquisition portion 15 by itself.

Because the insertion portion 2 is inserted into a narrow space, it is preferable for the dimensions of the outer diameter to be as small as is practical. The various types of electronic instruments that are placed inside the insertion portion 2 are provided in positions adjacent to each other. Because of this, in order for the entire insertion portion 2 to satisfy the requirements demanded of an intrinsically safe explosion-proof construction, it is necessary to consider the possibility of short-circuiting occurring between the electronic instruments (i.e., in the present embodiment, the illumination portion 7 and the image acquisition portion 15) of the plurality of systems that are provided inside the insertion portion 2.

In the endoscope 1 of the present embodiment, as is shown in FIG. 3, the insulating covering component 29 is placed between the illumination portion 7 and the image acquisition portion 15. Moreover, because the insulating covering component 29 is provided such that it extends over the entire length of the insertion portion 2 from the distal end 2a to the proximal end 2b thereof, within the range of the requirements needed to satisfy an intrinsically safe explosion-proof construction, it can be considered that no short-circuiting will occur between the illumination portion 7 and the image acquisition portion 15 at any point along the length of the insertion portion 2. In the present embodiment, because the sole electronic instruments provided in the insertion portion 2 are the illumination portion 7 and the image acquisition portion 15, the entire insertion portion 2 conforms to an intrinsically safe explosion-proof construction (Exia) standards.

As has been described above, according to the endoscope 1 of the present embodiment, because insulation that can be considered sufficient to prevent short-circuiting occurring between the illumination portion 7 and the image acquisition portion 15 is provided by the insulating covering component 29, the endoscope 1 can be safely used in an explosive atmosphere.

In an insertion portion inside which a plurality of electronic instruments are provided, if the possibility that short-circuiting might occur between the plurality of electronic instruments were to be considered, then thought may be given to limiting the amount of power supplied using as a reference the peak of the power that would be supplied to the electronic instruments if short-circuiting did occur. However, in this case, it is necessary for the design to take into account the possibility that the sum of the peaks of the power supplied to each electronic instrument might be supplied to a single electronic instrument. Because of this, the level of design freedom is low when designing a circuit whose purpose is to allocate sufficient power to each electronic circuit, and there is a possibility that the performance of the endoscope 1 will deteriorate due to insufficient power.

In contrast to this, in the endoscope 1 of the present embodiment, because it is possible to assume that short-circuiting will not occur between a plurality of electronic instruments (namely, in the case of the present embodiment, the illumination portion 7 and the image acquisition portion 15) whose drive power supply systems are mutually different, it is possible, within a range whereby the electronic instruments of each system individually satisfy by themselves the requirements of an intrinsically safe explosion-proof construction, to design the circuitry independently for each system. As a result, it is possible to prevent the performance of the endoscope 1 from deteriorating.

Modified Example 1

Next, a modified example of the endoscope 1 described in the first embodiment will be described. Note that, in the respective modified examples and embodiments described below, component elements that are the same as component elements described in the first embodiment are given the same symbols and any duplicated description thereof is omitted.

Figure 5:
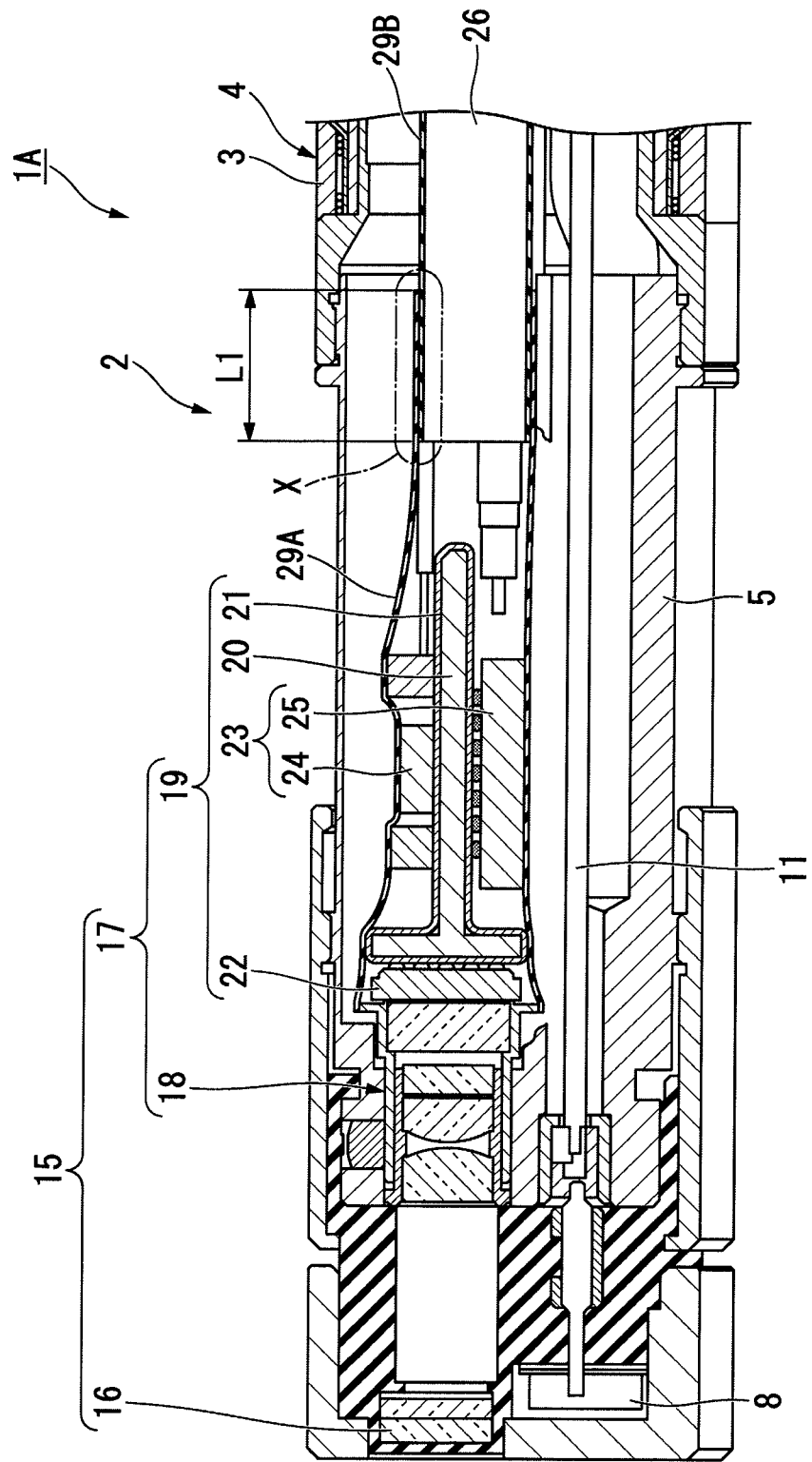
FIG. 5 is a cross-sectional view taken along the same cross-section as the line A-A in FIG. 2 showing an endoscope according to a modified example of the same embodiment.
Figure 6:
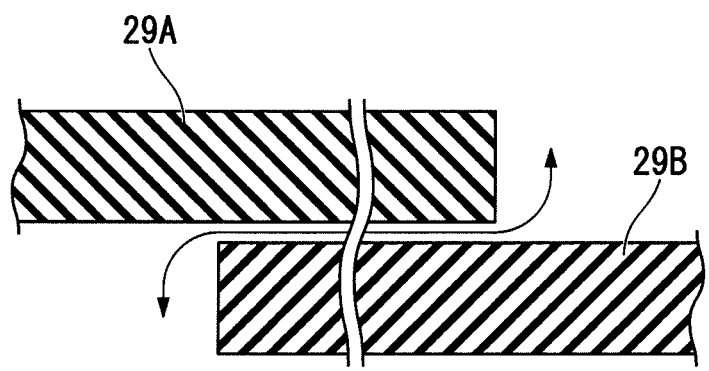
FIG. 6 is an enlarged cross-sectional view showing an enlargement of a portion of FIG. 5.

FIG. 5 is a cross-sectional view showing an endoscope 1A of the present modified example taken along the same cross-section as the line A-A in FIG. 2. FIG. 6 is an enlarged cross-sectional view of the portion indicated by the symbol X in FIG. 5.

As is shown in FIG. 5, instead of the above-described insulating covering component 29, the endoscope 1A of the present modified example has a first insulating component 29A that covers the entire circumference of the imaging unit 17 of the image acquisition portion 15, and a second insulating component 29B that covers the entire circumference of the wiring 26 of the image acquisition portion 15.

Both the first insulating component 29A and the second insulating component 29B are formed by heat-shrinkable tubes. Furthermore, the second insulating component 29B overlaps with the first insulating component 29A in the thickness direction of the first insulating component 29A. In the present embodiment, the first insulating component 29A covers the second insulating component 29B so as to be in contact with an outer circumferential surface of the second insulating component 29B.

As is shown in FIG. 5 and FIG. 6, the shape of the area where the first insulating component 29A and the second insulating component 29B mutually overlap is set based on the drive power that is supplied to the illumination portion 7 and the image acquisition portion 15 respectively. Specifically, assuming that the interiors of the first insulating component 29A and the second insulating component 29B, and the exteriors of the first insulating component 29A and the second insulating component 29B are in open communication with each other, the spatial distance through the gap between the first insulating component 29A and the second insulating component 29B, or a separation distance that is based on a creepage distance along the outer surfaces of the first insulating component 29A and second insulating component 29B are set so as to meet the requirements demanded of an intrinsically safe explosion-proof construction (Exia). More specifically, when the peak of the higher voltage out of the respective drive voltages of the light-emitting unit 8 and the imaging unit 17 is not more than 10V, then the first insulating component 29A and the second insulating component 29B mutually overlap such that the shortest distance measured along the contact surfaces of the first insulating component and the second insulating component is not less than 1.5 mm.

Note that in the present modified example as well, in the same way as in the above-described embodiment, the peak of the voltage supplied to the light-emitting unit 8 is set to 6.2V and the peak of the drive voltage supplied to the imaging unit 17 is set to 7.5V.

In the present modified example, the entire circumference of the insertion portion 2 from the distal end 2a to the proximal end 2b thereof is covered by an insulating component, namely, by the first insulating component 29A and the second insulating component 29B. Because of this, in the same way as in the endoscope 1 described in the foregoing first embodiment, the insertion portion 2 of the endoscope 1A of the present modified example conforms to intrinsically safe explosion-proof construction (Exia) standards.

Moreover, because the component covering the imaging unit 17 and the component covering the wiring 26 are separate components, assembling these together is easier than attaching the insulating covering component 29 described in the foregoing first embodiment.

Modified Example 2

Next, another modified example of the above-described first embodiment will be described.

Figure 7:
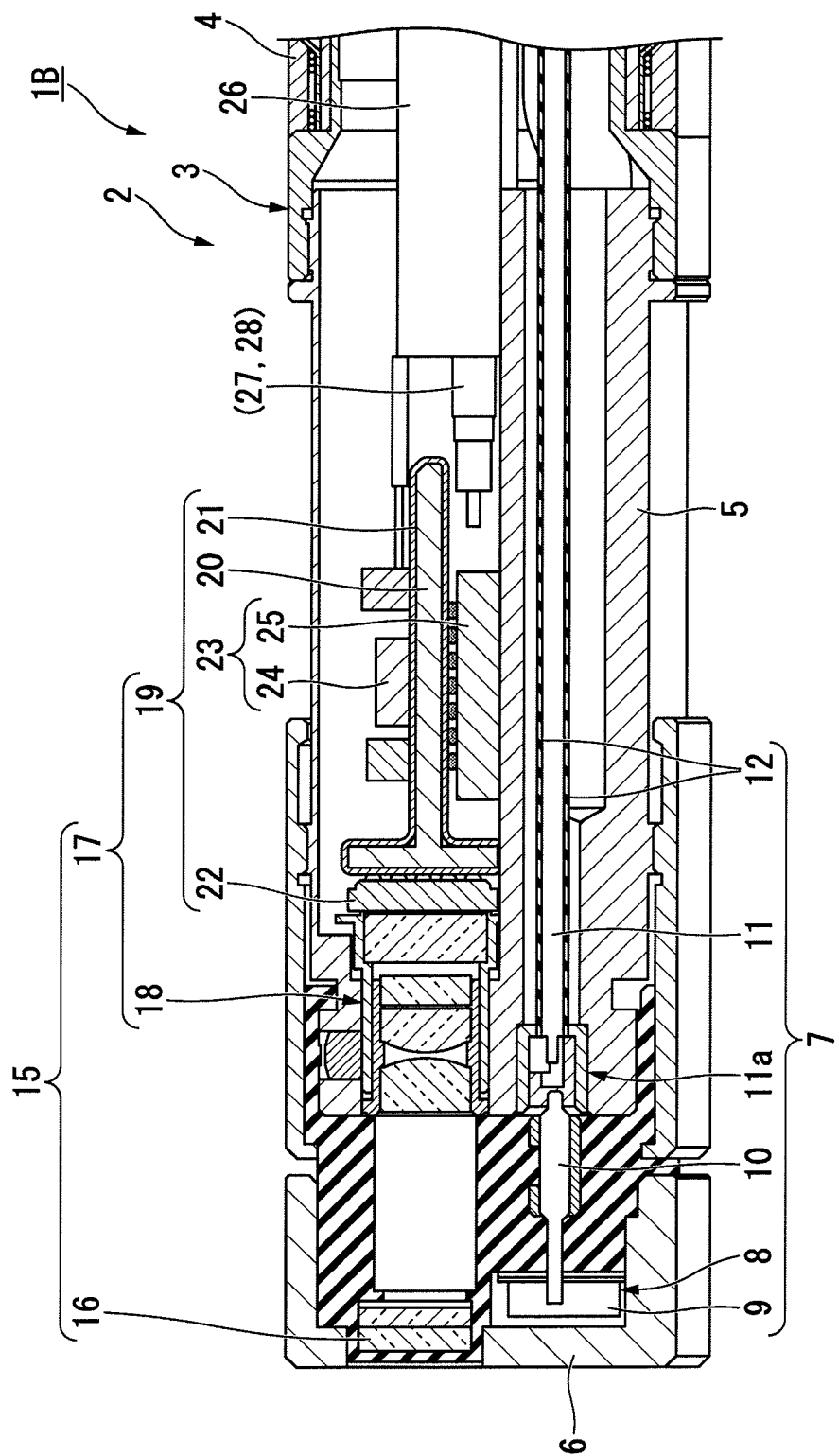
FIG. 7 is a cross-sectional view taken along the same cross-section as the line A-A in FIG. 2 showing an endoscope according to another modified example of the same embodiment.

FIG. 7 is a cross-sectional view showing an endoscope 1B of the present modified example taken along the same cross-section as the line A-A in FIG. 2.

As is shown in FIG. 7, in the present modified example, instead of the insulating covering component 29, an insulating covering component 12 that covers the wiring 11 and connecting terminal 11a of the illumination portion 7 is provided.

In the same way as the above-described insulating covering component 29, the thickness of the insulating covering component 12 is set based on the drive voltage that is supplied to the illumination portion 7 and the image acquisition portion 15.

In the case of the present modified example, the cross-sectional area of the insulating covering component 12 when viewed from the direction of the central axis of the endoscope 1 is smaller compared with when the entire imaging unit 17 is covered, as is the case in the first embodiment. Namely, in the case of the present modified example, the volume occupied by the insulating covering component 12 within the insertion portion 2 is smaller than the volume occupied by the insulating covering component 29.

Because of this, in a structure in which the insulating covering component 12 is provided near the illumination portion 7 instead of the insulating covering component 29 being provided near the image acquisition portion 15, the diameter of the insertion portion 2 can be made narrower while the same intrinsically safe explosion-proof construction is still guaranteed. Moreover, the bending performance thereof can be improved.

Modified Example 3

Next, yet another modified example of the above-described first embodiment will be described.

Figure 8:
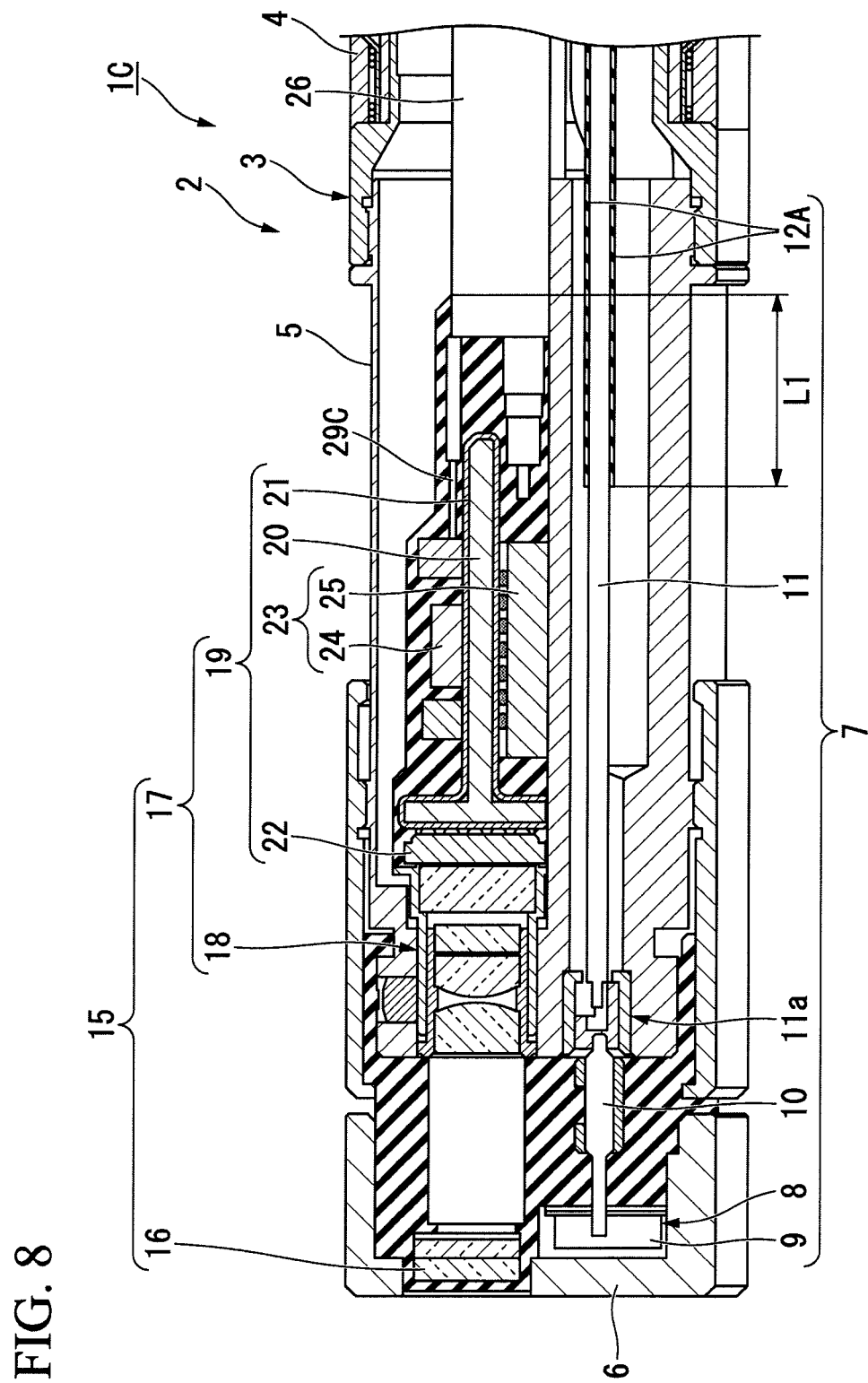
FIG. 8 is a cross-sectional view taken along the same cross-section as the line A-A in FIG. 2 showing an endoscope according to yet another modified example of the same embodiment.

FIG. 8 is a cross-sectional view showing an endoscope 1C of the present modified example taken along the same cross-section as the line A-A in FIG. 2.

As is shown in FIG. 8, the imaging unit 17 of the image acquisition portion 15 is covered over its entire circumference with a resin packing material, and an insulating covering component 12A covers the wiring 11 of the illumination portion 7 such that a portion thereof overlaps with the imaging unit 17 in the direction of the central axis of the insertion portion 2.

The resin used to cover the imaging unit 17 (hereinafter, referred to as 'packing resin 29C') is set such that the shortest distance between the external surface of the packing resin 29C and the external surface of the imaging unit 17 is the substantially same as the thickness of the insulating covering component 29 described in the foregoing first embodiment.

The insulating covering component 12A covering the wiring 11 of the illumination portion 7 has substantially the same thickness as the insulating covering component 12 described in the foregoing second embodiment.

In the same way as in the above-described Modified example 1, the length in the direction of the central axis of the insertion portion 2 that the packing resin 29C overlaps with the insulating covering component 12A is set such that the spatial distance through the gap between the packing resin 29C and the insulating covering component 12A, or the creepage distance along the outer surfaces of the packing resin 29C and the insulating covering component 12A satisfy the requirements demanded of an intrinsically safe explosion-proof construction (Exia).

In this type of structure as well, it can be considered that no short-circuiting will occur within the range of the requirements demanded by an intrinsically safe explosion-proof construction (Exia) between the illumination portion 7 and the image acquisition portion 15, and the entire insertion portion 2 conforms to intrinsically safe explosion-proof construction (Exia) standards.

Moreover, depending on how they are combined together, the thicknesses of the insulating covering component 29, the first insulating component 29A, the second insulating component 29B, the insulating covering component 12, the insulating covering component 12A, and the packing resin 29C described in the first embodiment and in the respective modified examples thereof may correspond to the resulting thicknesses when these components are added together. Furthermore, the wiring 26 and the wiring 11 may also be covered by an insulating material, and the thickness of this insulating material may also be added to the aforementioned thicknesses.

Second Embodiment

Next, an endoscope 50 according to a second embodiment of the present invention will be described.

Figure 9:
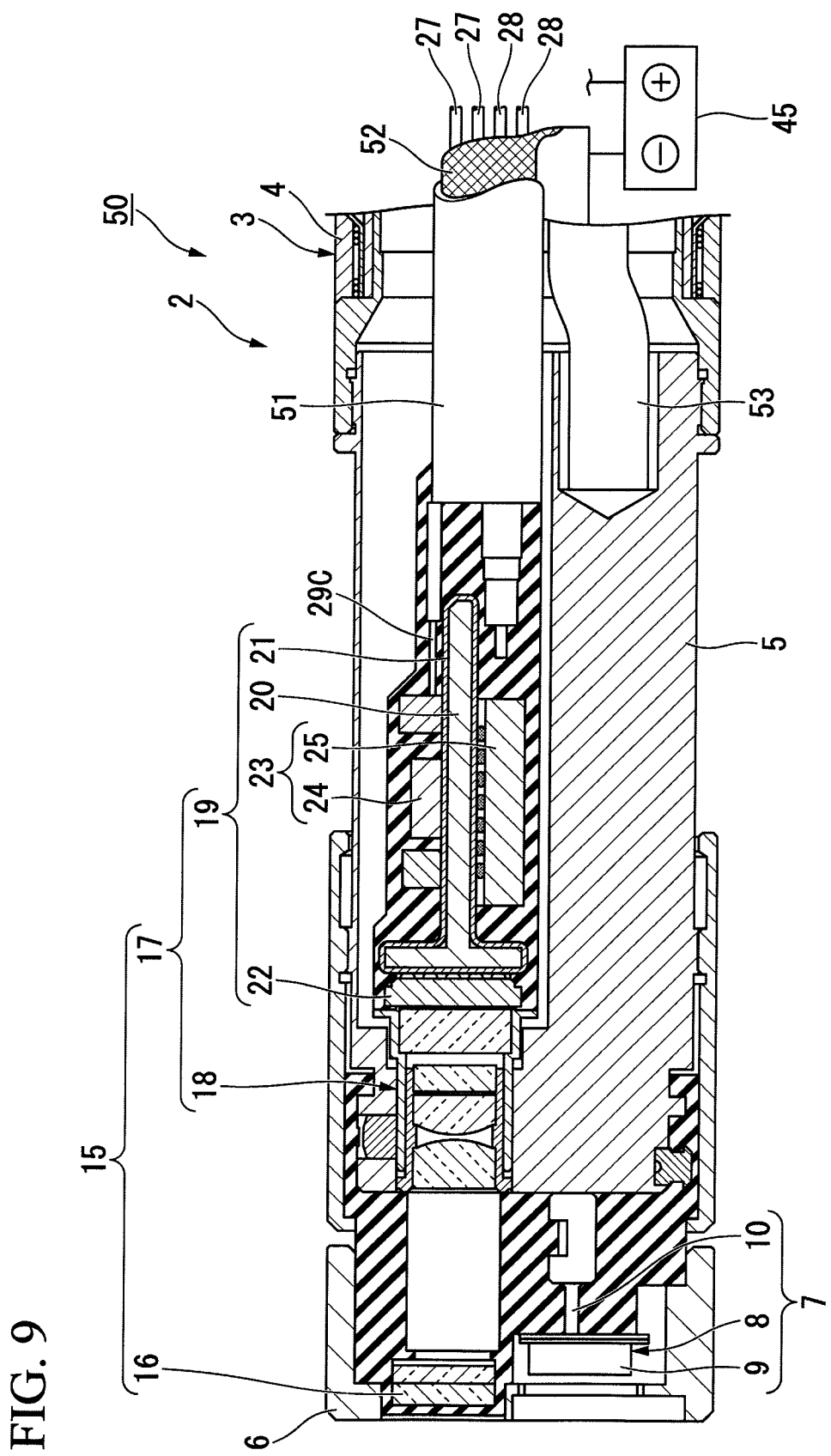
FIG. 9 is a cross-sectional view taken along the same cross-section as a line B-B in FIG. 2 showing an endoscope according to a second embodiment of the present invention.
Figure 10:
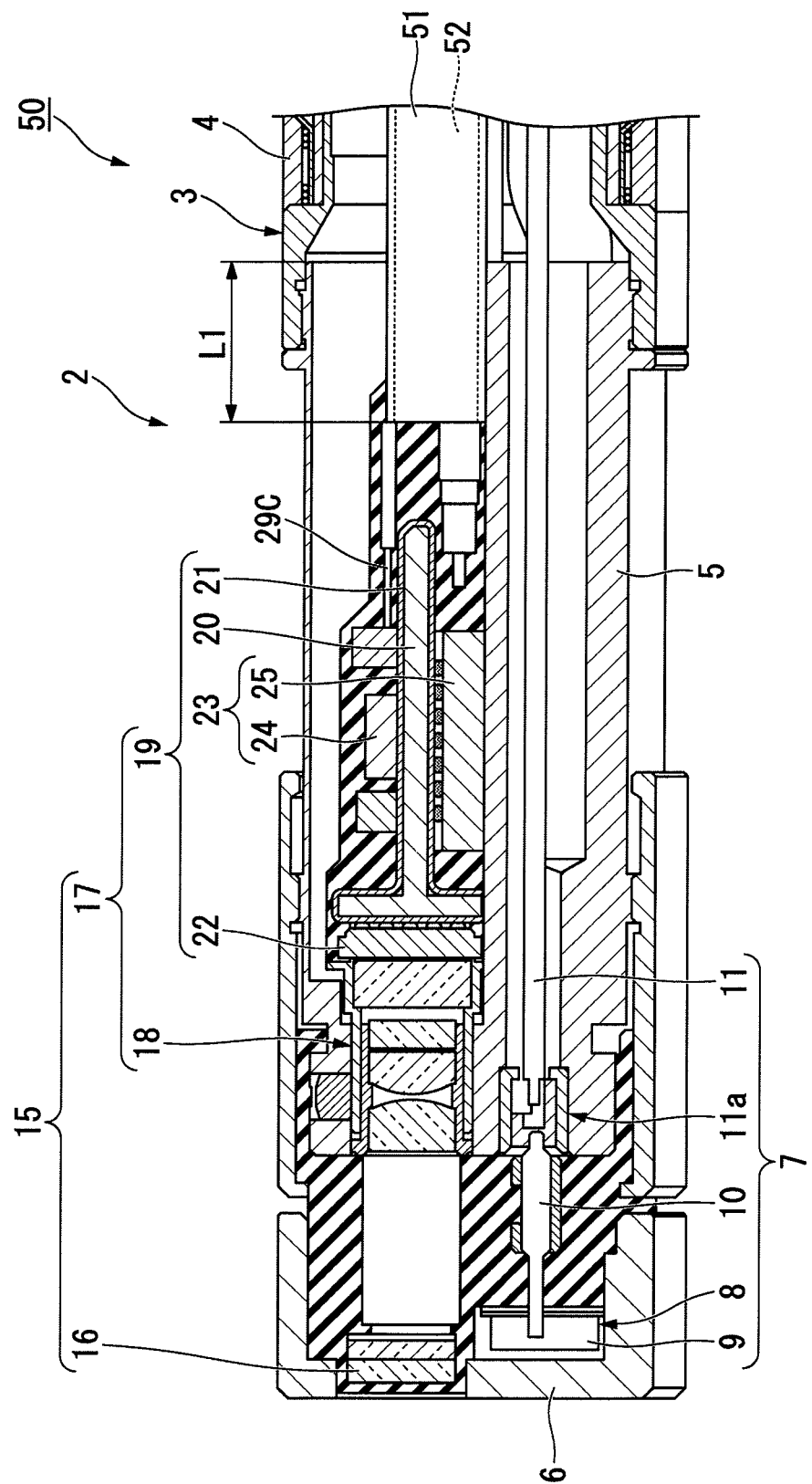
FIG. 10 is a cross-sectional view taken along the same cross-section as the line A-A in FIG. 2 showing the endoscope.

FIG. 9 is a cross-sectional view showing the endoscope 50 of the present embodiment taken along the same cross-section as the line B-B in FIG. 2. FIG. 10 is a cross-sectional view showing the endoscope 50 of the present embodiment taken along the same cross-section as the line A-A in FIG. 2.

Instead of preventing short-circuiting between the illumination portion 7 and the image acquisition portion 15 by means of an insulating component, in the endoscope 50 of the present embodiment, short-circuiting between the illumination portion 7 and the image acquisition portion 15 is prevented by a ground wire that is interposed in a non-contacting state between the illumination portion 7 and the image acquisition portion 15.

The endoscope 50 has the insertion portion 2, the main unit 40, the light-emitting unit 8, the wiring 11, the imaging unit 17, and the power limiting portions 14 and 33 and, in these respects, is the same as the endoscope 1 described in the foregoing first embodiment.

As is shown in FIG. 9, in the present embodiment, the imaging unit 17 is connected to wiring 51 that is different from the wiring 26. The wiring 51 has a structure in which an electricity wire 27 and a signal wire 28 are inserted inside a shield 52 that is formed by a woven tube in which a fine wire material made, for example, from metal has been woven, and the shield 52 is connected to the negative terminal of the battery 45 inside the main unit 40. Namely, the shield 52 functions as a ground wire whose ground potential is common to both the illumination portion 7 and the image acquisition portion 15.

Furthermore, in the present embodiment, the distal end rigid component 5 is made from metal, and a heat discharge wire 53 that is both thermally conductive and electrically conductive is provided in the distal end rigid component 5.

The heat discharge wire 53 is formed by a continuous metal wire whose distal end is fixed to the distal end rigid component 5 and whose proximal end is placed inside the main unit 40, and has the function of diffusing heat that is generated in the distal end of the insertion portion 2 to the proximal portion of the insertion portion 2. Furthermore, in the present embodiment, a proximal end of the heat discharge wire 53 is connected to the negative terminal of the battery 45 inside the main unit 40. Namely, the distal end rigid component 5 and the heat discharge wire 53 function as ground wires whose ground potential is common to both the illumination portion 7 and the image acquisition portion 15.

In the present embodiment, the distal end rigid component 5, the heat discharge wire 53, and the shield 52 function as system separating components that electrically separate the illumination portion 7 and the image acquisition portion 15 such that they comply with intrinsically safe explosion-proof construction standards.

Namely, any electricity that tries to flow from the illumination portion 7 to the image acquisition portion 15, and any electricity that tries to flow from the image acquisition portion 15 to the illumination portion 7 ends up flowing to the distal end rigid component 5, the heat discharge wire 53, and the shield 52 that are interposed between the illumination portion 7 and the image acquisition portion 15, and is returned to the negative terminal of the battery 45.

Furthermore, as is shown in FIG. 10, because the shield 52 of the wiring 51 and the distal end rigid component 5 overlap with each other in the direction of the central axis of the flexible portion 3, it can be assumed that no short-circuiting will occur between the wiring 11 of the illumination portion 7 and the wiring 51 of the image acquisition portion 15.

Because of this, the drive power supplied to the light-emitting unit 8 does not get supplied to the imaging unit 17, and nor does the drive power supplied to the imaging unit 17 get supplied to the light-emitting unit 8. Accordingly, in the endoscope 50 of the present embodiment as well, in the same way as the endoscopes 1, 1A, 1B, and 1C of the above-described first embodiment and the respective modified examples thereof, the insertion portion 2 conforms to intrinsically safe explosion-proof construction (Exia) standards.

Moreover, in the above-described first embodiment and the respective modified examples thereof, a structure is employed in which an insulating covering having a particular thickness is interposed between the illumination portion 7 and the image acquisition portion 15, however, in the present embodiment, because it is not necessary to provide a separate insulating covering, the dimensions of the outer diameter of the insertion portion 2 can be reduced. The bending performance thereof can also be improved.

Moreover, it is also possible for the shield 52 to be electrically connected to the ground of the imaging unit 17.

It is also possible for the heat discharge wire 53 to be electrically connected to the ground of the imaging unit 17 via the distal end rigid component 5.

It is also possible for the heat discharge wire 53 to be electrically connected to the negative polarity wiring and to the ground of the light-emitting unit 8 of the illumination portion 7.

Figure 11:
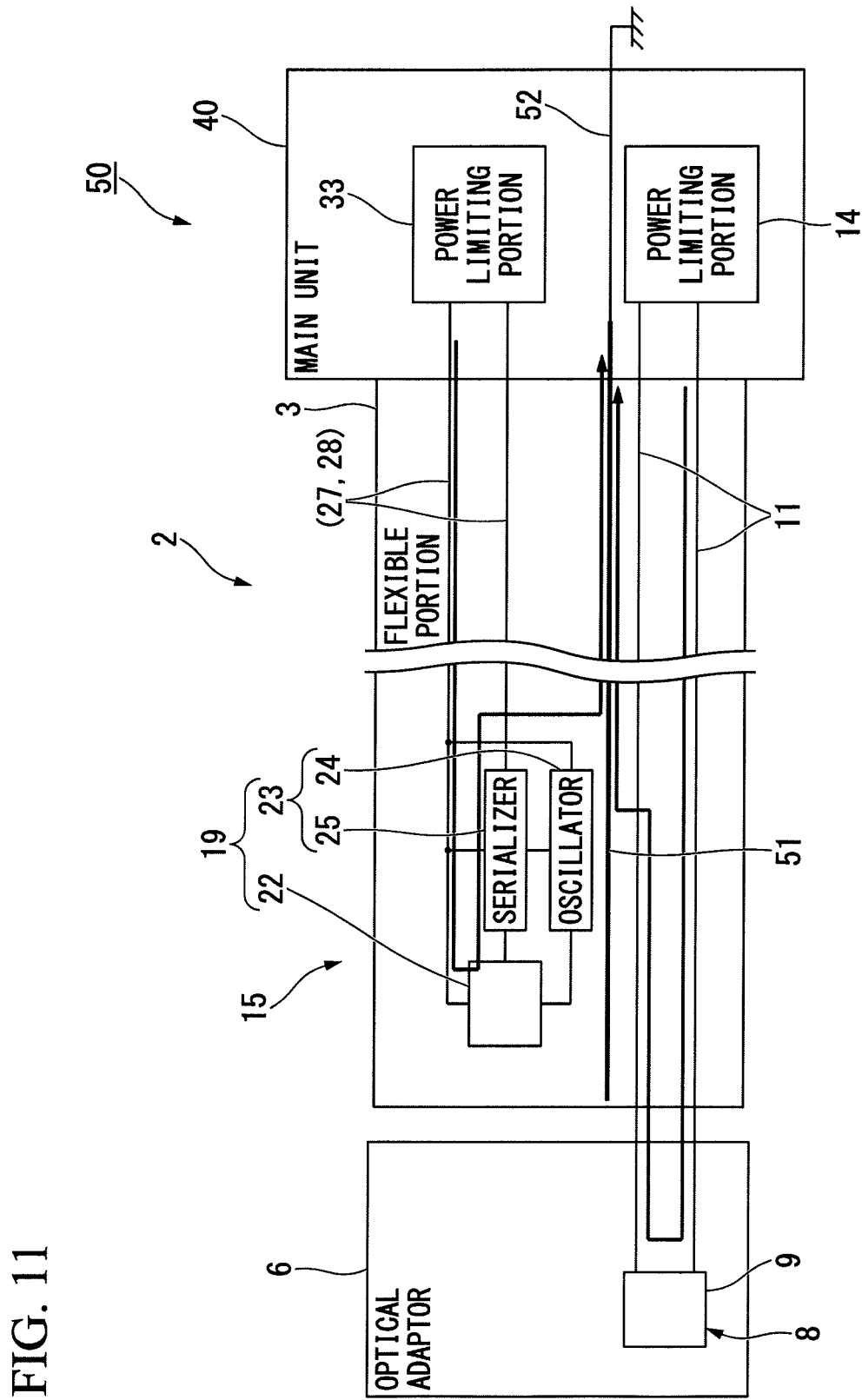
FIG. 11 is a block diagram showing the schematic structure of another structural example of the endoscope.

Moreover, in the present embodiment, an example is illustrated in which the shield 52, which forms a ground wire, and the heat discharge wire 53 are connected to the negative terminal of the battery 45, however, as is shown in FIG. 11 it is also possible for the ground wire to be earthed. For example, if the structure of the above-described second embodiment is applied to an endoscope that is driven by a mains power supply, then the ground wire can be electrically connected to the earth terminal of the main power supply instead of to the battery.

Modified Example 4

Next, a modified example of the above-describe endoscope 50 will be described.

Figure 12:
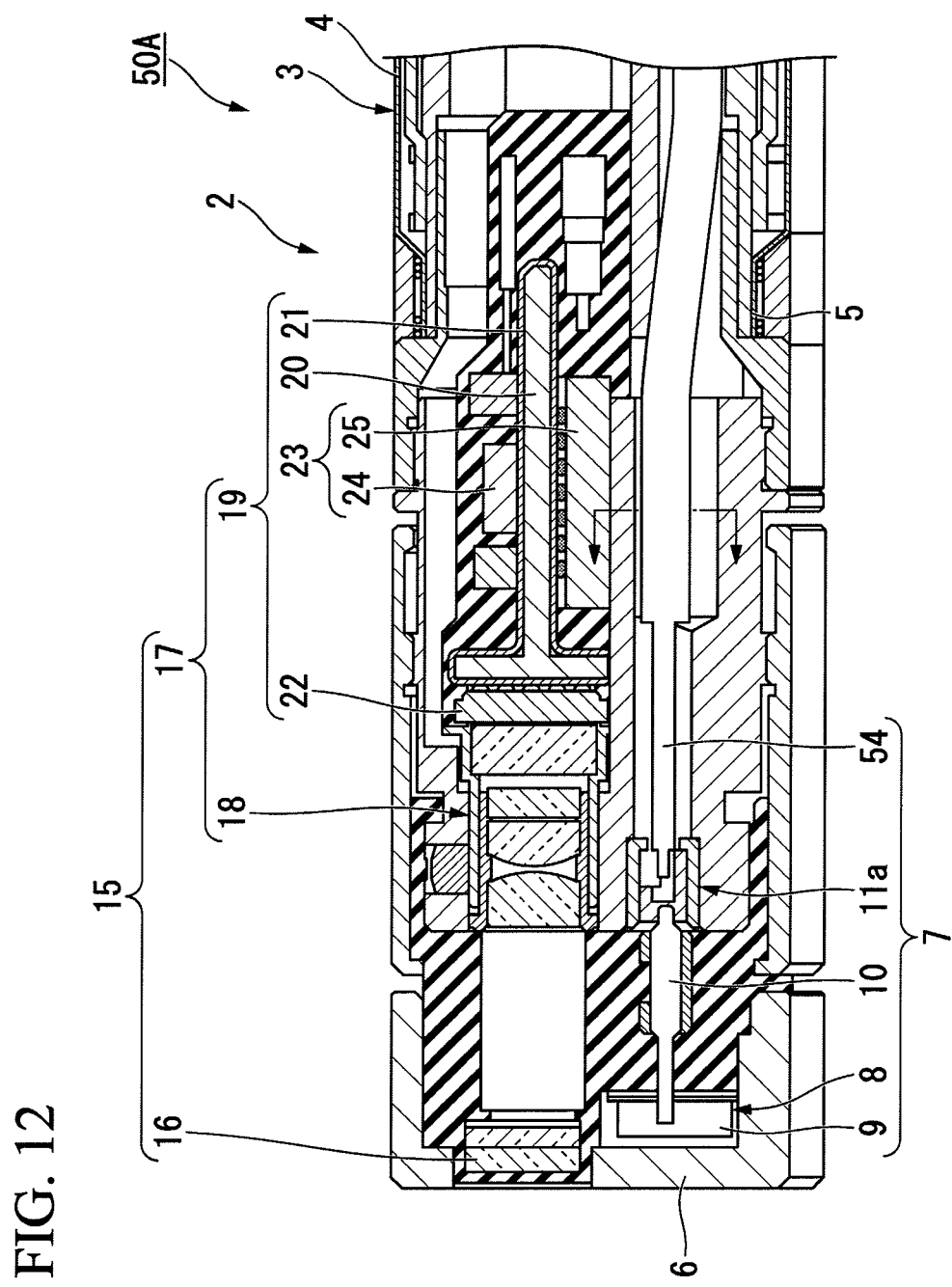
FIG. 12 is a cross-sectional view taken along the same cross-section as the line A-A in FIG. 2 showing an endoscope according to a modified example of the same embodiment.
Figure 13:
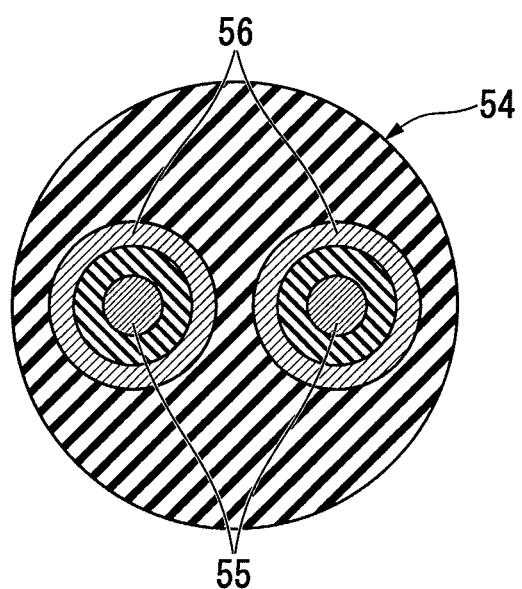
FIG. 13 is a cross-sectional view taken along a line C-C in FIG. 12.

FIG. 12 is a cross-sectional view showing an endoscope 50A of the present modified example taken along the same cross-section as the line A-A in FIG. 2. FIG. 13 is a cross-sectional view taken along a line C-C in FIG. 12.

As is shown in FIG. 12 and FIG. 13, the present modified example differs in that it has wiring 54 whose structure is different from that of the wiring 11 that was described in the foregoing first embodiment and their respective modified examples thereof, and in the foregoing second embodiment. Moreover, in the present modified example, the shield 52 described in the foregoing second embodiment is not provided.

The wiring 54 provided in the illumination portion 7 has a pair of electricity wires 55 that are used to supply drive power to the light-emitting unit 8, a shield 56 that covers the respective electricity wires 55 via an insulating material, and an insulating tube that further covers the shield 56. The pair of electricity wires 55 are connected to the battery 45 via the illumination control unit 13, and power that is limited by the power limiting portion 14 of the illumination control unit 13 is supplied to the pair of electricity wires 55.

In the same way as the above-described shield 52 that is provided in the wiring of the image acquisition portion 15, the shield 56 may be formed in a woven tube shape that is woven from a metal fine-wire material, or in a horizontally wound shape in which fine wires have been laid side-by-side with each other, and the shield 56 is connected to the negative terminal of the battery 45 inside the main unit 40.

In the present modified example, instead of the shield 52 that is provided in the wiring of the image acquisition portion 15, the shield 56 is provided in the wiring 54 of the illumination portion 7. Consequently, the cross-sectional area of the shield 56 as viewed in the direction of the central axis of the insertion portion 2 is smaller than when the shield 52 is provided in the wiring 51 of the image acquisition portion 15. As a result, in the case of the present modified example, because the volume occupied by the shield 56 within the insertion portion 2 is smaller than the volume occupied by the shield 52 that is described in the foregoing second embodiment, it is possible to reduce the dimensions of the outer diameter of the insertion portion 2. It is also possible to improve the bending performance thereof.

Moreover, in the present modified example, the position of the distal end of the shield 56 that is provided on the wiring 54 of the illumination portion 7 is located further to the distal portion of the insertion portion 2 than is the position of the distal end of the shield 52 when the shield 52 is provided on the wiring 51 of the image acquisition portion 15. Accordingly, the distal end rigid component 5 can be shortened in the direction of the central axis of the insertion portion 2, so that the length of the distal end rigid portion of the insertion portion 2 can also be shortened. As a result of this, the ease which with the insertion portion 2 can be inserted into a subject can be improved.

Note that in FIG. 13, an example in which the shields 56 of a pair of electricity wires 55 are connected to the negative terminal of the battery 45 within the main unit 40 is shown, however, it is also possible to only provide a shield on the positive side (i.e., on the anode side) of the electricity wires 55, and to connect this to the negative terminal of the battery 45 within the main unit 40.

Modified Example 5

Next, yet another modified example of the above-described modified example 4 will be described.

Figure 14:
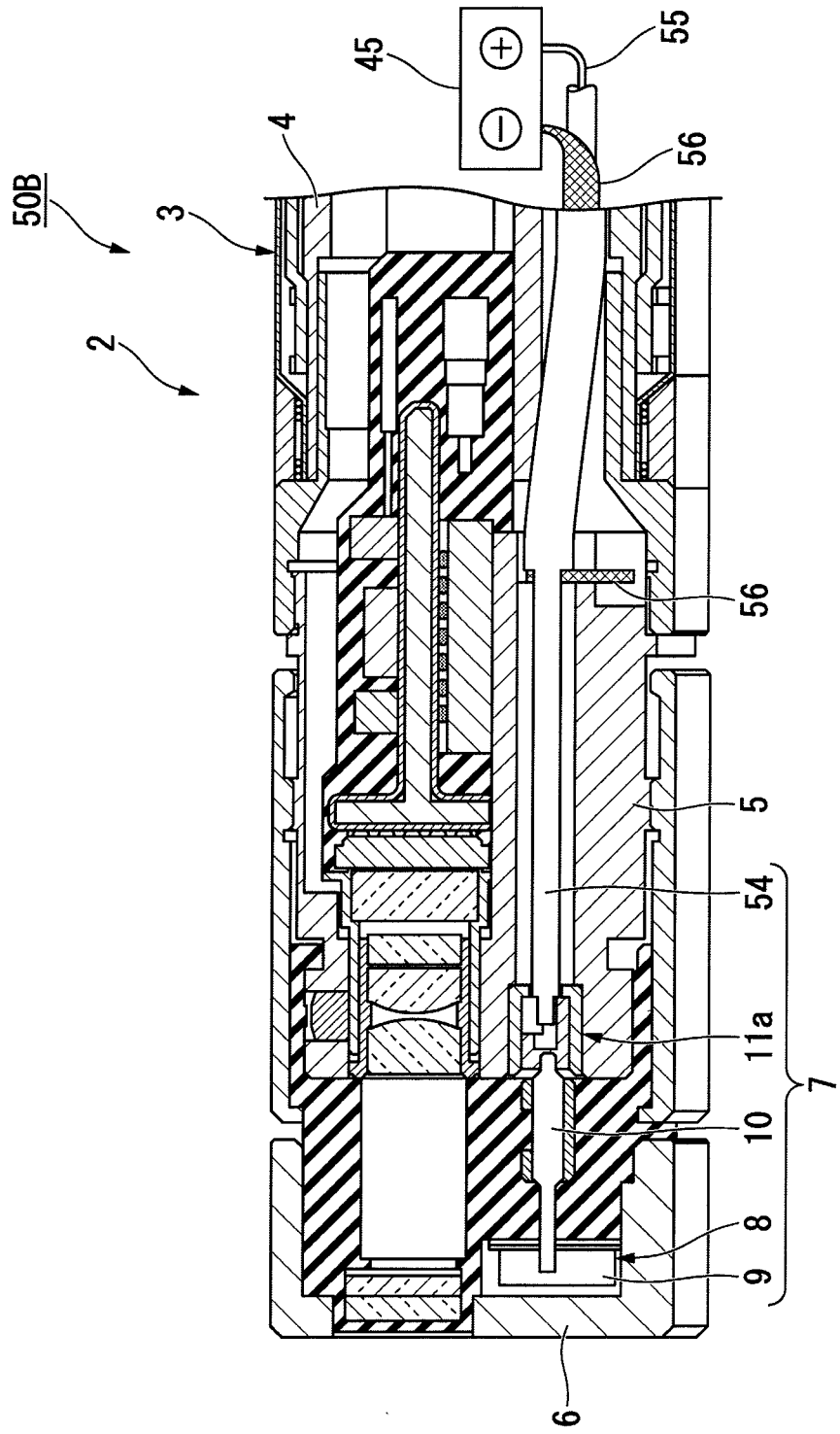
FIG. 14 is a cross-sectional view taken along the same cross-section as the line A-A in FIG. 2 showing an endoscope according to another modified example of the same embodiment.

FIG. 14 is a cross-sectional view showing an endoscope 50B of the present modified example taken along the same cross-section as the line A-A in FIG. 2.

As is shown in FIG. 14, in the present modified example, the shield 56 that is provided on the wiring 54 of the illumination portion 7 functions as the above-described ground wire that is connected to the distal end rigid component 5. Moreover, in the present modified example, the heat discharge wire 53 is not provided, and heat that is generated at the distal inside of the insertion portion 2 is diffused towards the proximal portion of the insertion portion 2 by the shield 56 that is provided on the wiring 54 of the illumination portion 7.

According to the endoscope 50B of the present modified example, the dimensions of the outer diameter of the insertion portion 2 can be further reduced compared to the structure of the above-describe modified example 4 due to the fact that it is not necessary to provide the heat discharge wire 53. Consequently, the bending performance can be further improved.

Third Embodiment

Next, an endoscope 60 according to a third embodiment of the present invention will be described.

Figure 15:
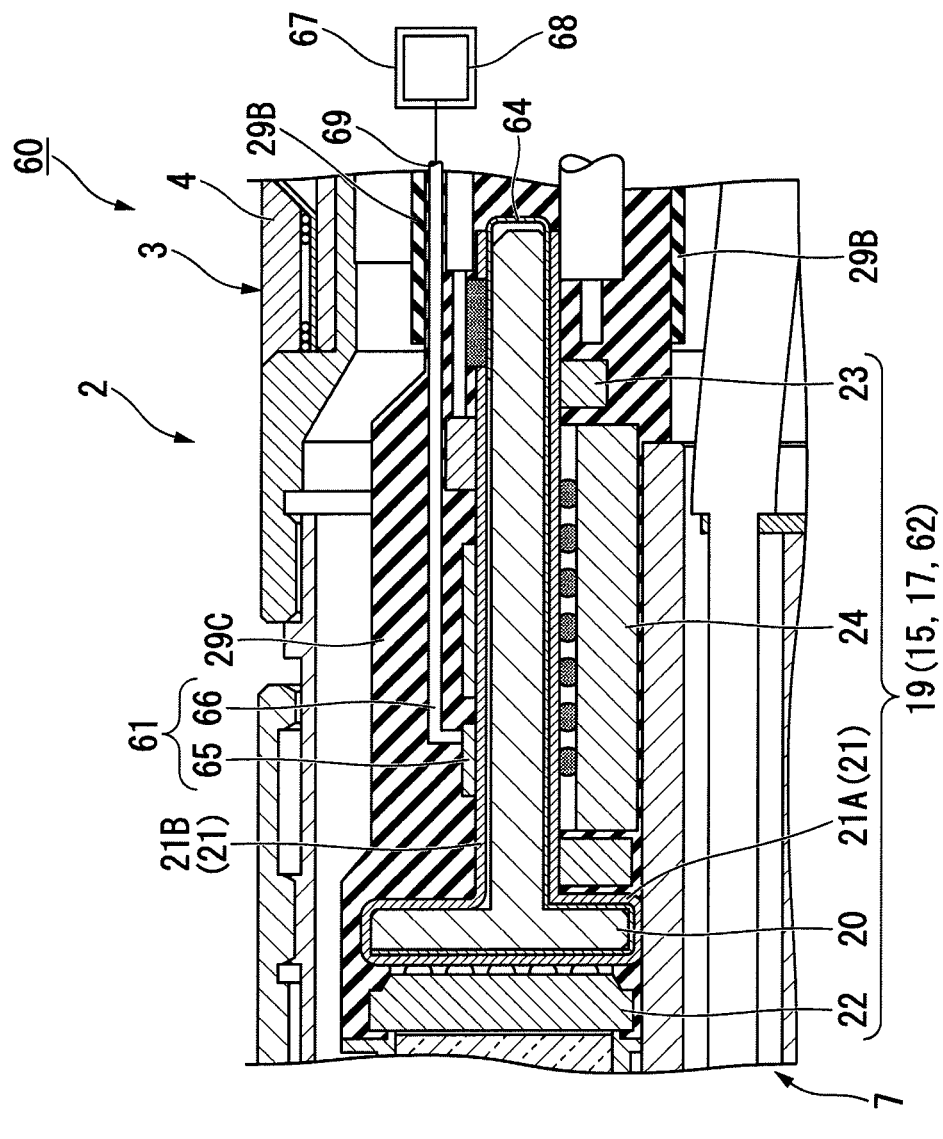
FIG. 15 is an enlarged cross-sectional view showing an imaging unit of an endoscope according to a third embodiment of the present invention.

FIG. 15 is an enlarged cross-sectional view showing an enlargement of the imaging unit 17 of the endoscope 60 of the present embodiment.

In addition to the illumination portion 7 and the image acquisition portion 15, the endoscope 60 of the present embodiment is further provided with an acceleration measuring portion 61, which is an electronic instrument that operates using drive power from a separate system.

The acceleration measurement portion 61 is packaged on the circuit substrate 21 of the imaging unit 17 such that it is electrically separated from the respective circuits making up the imaging unit 17. Although the circuit substrate 21 of the imaging unit 17 is a single continuous flexible substrate, hereinafter, the portion where the respective electronic components belonging to the image acquisition portion 15 (these will be referred to below as 'first electronic components 62') are packaged is referred to as a first substrate 21A, while a portion where the respective electronic components belonging to the acceleration measurement portion 61 (hereinafter, these will be referred to as 'second electronic components 63') are packaged is referred to as a second substrate 21B.

In the present embodiment, the first substrate 21A and the second substrate 21B are arranged in parallel with each other with the supporting body 20 interposed between them. The first electronic components 62 that are packaged on the first substrate 21A and the second electronic components 63 that are packaged on the second substrate 21B are arranged symmetrically to each other such that their component surfaces (i.e., the surfaces thereof where the ground or pins that are used for connecting to the circuit substrate 21 are provided) are opposite each other when the circuit substrate 21 is folded in half.

The first substrate 21A is a multilayered substrate having a first layer on which the wiring pattern of the imaging unit 17 is formed and a second layer on which a solid ground pattern 64 is formed. The solid ground pattern 64 provided on the first substrate 21A is connected to the ground wire from among the wiring 26 of the image acquisition portion 15.

The acceleration measurement portion 61 is provided with an acceleration sensor 65 which is a portion of the second electronic components 63 that are packaged on the second substrate 21B of the circuit substrate 21, wiring 66 that is connected to the acceleration sensor 65 and extends from the distal end of the insertion portion 2 to the proximal end thereof, and a sensor control unit 67 that is connected to wiring inside the main unit.

The acceleration sensor 65 is a sensor that detects the acceleration acting on the insertion portion 2 when the distal end of the insertion portion 2 is being moved.

The sensor control unit 67 is an electronic circuit that is driven by power supplied from a battery, and refers to the value of the acceleration detected by the acceleration sensor 65 and then delivers this value to a main control unit. In addition, the sensor control unit 67 has a power limiting portion 68 that, when the acceleration sensor 65 is in a normal state, or when it is in a malfunctioning state, limits the supplied drive power, and the illumination portion 7, the image acquisition portion 15, and the acceleration measurement portion 61 operate by being supplied with drive power from mutually separate systems.

An insulating covering component 69 having the same type of structure as that described in the first embodiment is provided on the wiring 66 of the acceleration measurement portion 61. Namely, in the present embodiment, of the electronic instruments of the three systems, namely, of the illumination portion 7, the image acquisition portion 15, and the acceleration measurement portion 61, the packing resin 29C, the second insulating component 29B, and the insulating covering component 69 that enable the insertion portion 2 to conform to the intrinsically safe explosion-proof construction (Exia) standards are provided in two systems, namely, in the image acquisition portion 15 and the acceleration measurement portion 61.

If insulating covering components that enable two of the three systems to conform to the intrinsically safe explosion-proof construction (Exia) standards are provided, then even if an insulating covering component is not provided on the remaining system, it can be assumed that short-circuiting will not occur between the electronic instruments of the three systems.

The ground pattern 64 (i.e., the second layer) that is formed on the first substrate 21A is interposed between the first electronic components 62 (for example, the imaging element 22, the oscillator 24, the serializer circuit 25, and other electronic components that are not shown) that belong to the image acquisition portion 15, and the second electronic components 63 (for example, the acceleration sensor 65 and other electronic components that are not shown) that belong to the acceleration measurement portion 61.

When the first substrate 21A is viewed from the thickness direction thereof, the ground pattern 64 extends over a broader range than a surface that is prescribed by an envelope curve surrounding all of the first electronic components 62. Moreover, in the present embodiment, a portion of the ground pattern 64 extends in a wall shape that partitions the imaging element 22 from the acceleration sensor 65.

In the endoscope 60 of the present embodiment, the electronic instruments of the three systems, namely, the illumination portion 7, the image acquisition portion 15, and the acceleration measurement portion 61 are provided inside the insertion portion 2. It can be assumed that short-circuiting will not occur between the illumination portion 7, the image acquisition portion 15, and the acceleration measurement portion 61 due to the insulating covering components being provided on the image acquisition portion 15 and the acceleration measurement portion 61.

Furthermore, because the solid ground pattern 64 is interposed between the acceleration sensor 65 that is provided on the circuit substrate 21 of the imaging unit 17 and the respective electronic circuits that belong to the image acquisition portion 15 on the circuit substrate 21, short-circuiting does not occur between the respective circuits belonging to the image acquisition portion 15 and the acceleration sensor 65 due to the same type of operational effects as those described in the foregoing second embodiment.

Moreover, when the circuit substrate 21 is viewed on a cross-section that is orthogonal to the longitudinal axis of the insertion portion 2, the separation distance between the acceleration sensor 65 that is provided on the circuit substrate 21 of the imaging unit 17 and the respective electronic circuits belonging to the image acquisition portion 15 on the circuit substrate 21 is set such that the shortest distance along the outer circumference of the solid ground pattern 64 satisfies the requirements demanded from an intrinsically safe exploration-proof construction (Exia).

Specifically, because the packing resin 29C is interposed around the periphery of the circuit substrate of the imaging unit 17, the resin packing separation distance is set such that the requirements demanded from an intrinsically safe exploration-proof construction (Exia) are satisfied.

According to the endoscope 60 of the present embodiment, because it can be assumed that short-circuiting will not occur between the illumination portion 7, the image acquisition portion 15, and the acceleration measurement portion 61 within the range of the requirements needed to satisfy an intrinsically safe explosion-proof construction (Exia), the entire insertion portion 2 conforms to intrinsically safe explosion-proof construction (Exia) standards.

Furthermore, because the solid ground pattern 64 is provided in the imaging unit 17, the effects of noise from the outside can be alleviated.

Moreover, in the first substrate 21A, the heat generated by the respective electronic components packaged on the first substrate 21A is diffused to a second layer (i.e., the solid ground pattern 64) via a first layer. As a result of this, it is possible to improve the heat discharge performance of the electronic components packaged on the first substrate 21A.

Note that an example in which the circuit substrate 21 is folded in half is shown in the above-describe third embodiment, however, it is also possible, for example, for the first electronic components 62 to be packaged on one surface in the thickness direction of a three layer substrate and for the second electronic components 63 to be packaged on the other surface thereof, and for the solid ground pattern 64 to be formed in an intermediate layer of this three layer substrate. In this case as well, because the solid ground pattern 64 is interposed between the first electronic components 62 and the second electronic components 63, the same type of effects can be achieved as in the above-described third embodiment. Note that, in this case, the circuit substrate 21 is not limited to being a flexible printed substrate, and may be, for example, a laminated glass epoxy substrate or a paper phenol substrate.

Modified Example 6

Figure 16:
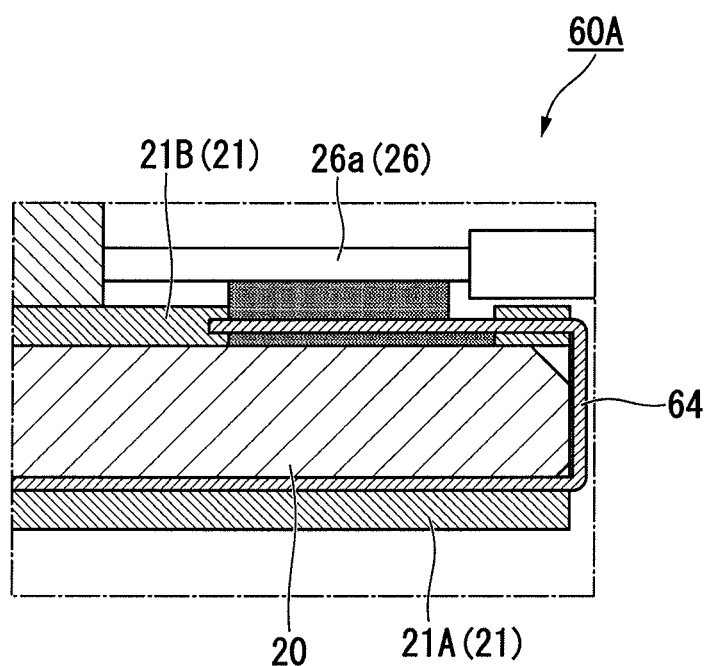
FIG. 16 is an enlarged cross-sectional view showing a portion of an imaging unit of an endoscope according to another modified example of the same embodiment.

Next, a modified example of the endoscope 60 described in the foregoing third embodiment will be described. FIG. 16 is a cross-sectional view showing an enlargement of a portion of the imaging unit 17 in an endoscope 60A of the present modified example.

The present modified example differs from those described above in that the supporting body 20 is formed from metal, and the solid ground pattern 64 and the supporting body 20 are connected together both thermally and electrically.

Specifically, the solid ground pattern 64, the supporting body 20, and a ground line 26a of the wiring 26 are connected together by solder. In the case of the present modified example, heat that has been diffused to the solid ground pattern 64 is further diffused to the supporting body 20. As a result of this, it is possible to improve even further the heat discharge performance of the electronic components packaged on the first substrate 21A.

Moreover, because the supporting body 20 is formed from metal and is electrically connected to the ground pattern 64, the supporting body 20 also functions as a ground. Because of this, in addition to the fact that short-circuiting is prevented by means of the same type of operating effects as those obtained from the ground pattern 64 described above in the foregoing third embodiment, the ground potential of the imaging unit 17 is further stabilized, and the quality of video signals transmitted from the imaging unit 17 to the imaging control unit 30 can be improved.

While preferred embodiments of the invention have been described and illustrated above, it should be understood that these are exemplary of the invention and are not to be considered as limiting. Additions, omissions, substitutions, and other modifications can be made without departing from the spirit or scope of the present invention.

Accordingly, the invention is not to be considered as limited by the foregoing description and is only limited by the scope of the appended claims.

What is claimed is:

1. An endoscope comprising:
an elongated insertion portion;
a main unit to which one end of the insertion portion is attached;
first electronic components that are provided inside the insertion portion;
second electronic components that are provided inside the insertion portion and are supplied with drive power from a separate system from that used for the first electronic components;
a first substrate having a length and a thickness, the thickness of the first substrate being less than the length of the first substrate, the first electronic components being packaged on a first surface of the first substrate;
a second substrate having a length and a thickness, the thickness of the second substrate being less than the length of the second substrate, the second electronic components being packaged on a first surface of the second substrate;
a plurality of power limiting portions that limit to a predetermined value or less a drive power that they supply to the first electronic components and the second electronic components respectively via mutually different systems;
a first wiring of which at least a portion is placed inside the insertion portion, and that electrically connects together one of the power limiting portions and the first electronic components and supplies the drive power to the first electronic components;
a second wiring of which at least a portion is placed inside the insertion portion, and that electrically connects together another of the power limiting portions and the second electronic components and supplies the drive power to the second electronic components; and
a solid ground pattern formed either on a second surface of the first substrate which is located opposite to the first surface of the first substrate or inside the first substrate and that, when viewed along the length of the first substrate, the solid ground pattern extends over a broader area than the first electronic components.

2. The endoscope according to claim 1, wherein:

the first substrate and the second substrate are integrated into a multi-layer substrate by mutually superimposing the first substrate and the second substrate in the thickness direction of the first and second substrates; and the ground pattern is interposed between the first electronic components and second electronic components.

3. The endoscope according to claim 1, wherein:

the first substrate and the second substrate are defined by first and second sections of a continuous flexible substrate located in the insertion portion;

the first electronic components and the second electronic components are packaged on the first and second sections of the continuous flexible substrate; and the flexible substrate is folded in half at a location between the first electronic components and the second electronic components such that the ground pattern is positioned between the first electronic components.

4. The endoscope according to claim 1, wherein:

a metal supporting body is provided at a distal end side of the insertion portion and supports the first substrate and the second substrate; and the ground of the first electronic components and the second electronic components is electrically connected to the supporting body; and the first electronic components and the second electronic components are thermally connected to the supporting body.

* * * * *